United States Patent [19]

Engel et al.

[11] Patent Number: 4,946,836
[45] Date of Patent: Aug. 7, 1990

[54] NITROGEN-CONTAINING CYCLO-ALIPHATIC COMPOUNDS HAVING AN AMINO RADICAL AND A PYRIDINE RADICAL

[75] Inventors: Jürgen Engel, Alzenau; Axel Kleemann, Mühlheim; Bernd Nickel, Mühltal; Istvan Szelenyi, Schwaig, all of Fed. Rep. of Germany

[73] Assignee: Asta Pharma AG, Frankfurt am Main, Fed. Rep. of Germany

[21] Appl. No.: 399,439

[22] Filed: Aug. 28, 1989

Related U.S. Application Data

[63] Continuation of Ser. No. 182,662, Apr. 18, 1988, abandoned.

[30] Foreign Application Priority Data

Apr. 18, 1987 [DE] Fed. Rep. of Germany ....... 3713246

[51] Int. Cl.$^5$ .................... A61K 31/55; C07D 401/12
[52] U.S. Cl. .................... 514/183; 514/212; 514/318; 514/339; 514/343; 514/344; 540/1; 540/481; 540/597; 546/187; 546/193; 546/273; 546/275; 546/278; 546/281
[58] Field of Search ................ 540/481, 597; 546/187, 546/193, 273, 275, 278, 281; 514/183, 212, 318, 339, 344, 343

[56] References Cited

U.S. PATENT DOCUMENTS 4,643,995 2/1987 Engel et al. .................... 540/481

Primary Examiner—Mary C. Lee
Assistant Examiner—Catherine S. Kilby Scalzo
Attorney, Agent, or Firm—Cushman, Darby & Cushman

[57] ABSTRACT

Compounds of formula

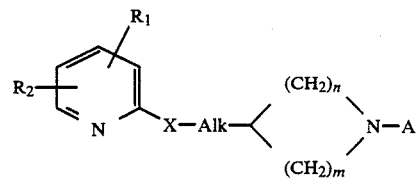

wherein the radicals $R_1$ and $R_2$ are the same or different and represent hydrogen, halogen atoms, a trifluoromethyl group, a cyano, a nitro group, an amino group, a mono-$C_1$–$C_6$-alkylamino group, a di-$C_1$–$C_6$-alkylamino group, an amino group that is substituted by a phenyl $C_1$–$C_4$-alkyl radical, a $C_2$–$C_6$-alkanoyl-amino group, a $C_1$–$C_6$-alkoxycarbonyl amino group, a $C_1$–$C_6$-alkyl group optionally substituted by a phenyl radical, a hydroxy group, a $C_1$–$C_6$-alkoxy group, a $C_2$–$C_6$-alkanoyloxy group, a phenoxy group or represent a carbamoyl group optionally substituted by one or two $C_1$–$C_6$-alkyl groups and the radical A is an acyl group which is derived from an amino acid as well as processes for their preparation.

3 Claims, No Drawings

NITROGEN-CONTAINING CYCLO-ALIPHATIC COMPOUNDS HAVING AN AMINO RADICAL AND A PYRIDINE RADICAL

This is a continuation on Ser. No. 182,662, filed 4/18/88, now abandoned.

The prevent invention relates to compounds having an analgesic effect which is long-lasting and have a delayed onset of action

BACKGROUND OF THE INVENTION

European patent application No. 0 149 088 describes analgesically active compounds having the formula

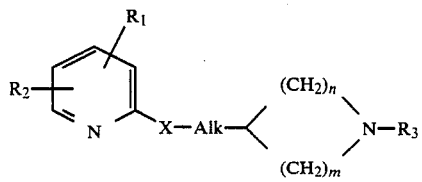

wherein the radicals $R_1$ and $R_2$ are the same or different and represent hydrogen, halogen atoms, a trifluoromethyl group, a cyano group, a nitro group, an amino group, a mono-$C_1$-$C_6$-alkylamino group, a di-$C_1$-$C_6$-alkylamino group, an amino group that is substituted by a phenyl radical, a mono or dihalogenphenyl radical or a phenyl-$C_1$-$C_4$-alkyl radical, a $C_1$-$C_6$-alkanoylamino group, a $C_1$-$C_6$-alkoxycarbonylamino group, a $C_1$-$C_6$-alkyl group optionally substituted by a phenyl radical, a phenyl group, a hydroxy group, a $C_1$-$C_6$-alkoxy group, a phenoxy group, a carboxy group, a carb-$C_1$-$C_6$-alkoxy group or a carbamoyl group optionally substituted by one or two $C_1$-$C_6$-alkyl groups, the radical $R_3$ is hydrogen, a $C_1$-$C_6$-alkyl group, a $C_3$-$C_6$-alkenyl group, a $C_3$-$C_6$-alkynyl group, a $C_3$-$C_7$-cycloalkyl group, a $C_5$-$C_7$-cycloalkenyl group, a phenyl-$C_1$-$C_4$-alkyl group, a carb-$C_1$-$C_6$-alkoxy group, a $C_2$-$C_6$-alkanoyl group optionally substituted by a $C_3$-$C_6$-cycloalkyl radical or a $C_1$-$C_4$-alkyl group which has at the same carbon atom two $C_1$-$C_6$-alkoxy groups or a $C_2$-$C_4$-alkylenedioxy group or wherein $R_3$ is a $C_1$-$C_6$-alkyl group which is substituted once or twice by $C_3$-$C_7$-cycloalkyl groups, hydroxy groups $C_1$-$C_6$-alkoxy groups, halogen atoms, sulfo groups (—SO$_3$H), amino groups, $C_1$-$C_6$-alkylamino groups, di-$C_1$-$C_6$-alkylamino groups, $C_1$-$C_6$-alkylcarbonyl groups, $C_3$-$C_7$-cycloalkylcarbonyl groups, carb-$C_1$-$C_6$-alkoxy groups or benzoyl groups, X represents oxygen, sulphur, SO or SO$_2$, Alk is alkylene with 0–4 carbon atoms and n and m are the same or different and can represent the numbers 1–3, wherein n can also be 0 when Alk is alkylene with at least one carbon atom and m in this case represents the numbers 2–6 and where the grouping

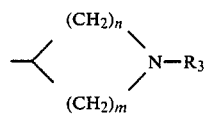

can also represent the quinuclidyl radical or the tropanyl radical.

SUMMARY OF THE INVENTION

The present invention is concerned with compounds which are pharmacologically active. In particular, the compounds of the invention have a pronounced and strong analgesic effect. Compared to previously known compounds, this analgesic effect is particularly long-acting and has a delayed onset of action.

The object of the invention is therefore to provide compounds with favorable pharmacological properties which can, for example, be used as analgesically active medicaments (in particular as delayed-release agents).

More specifically, the invention is concerned with compounds of the formula:

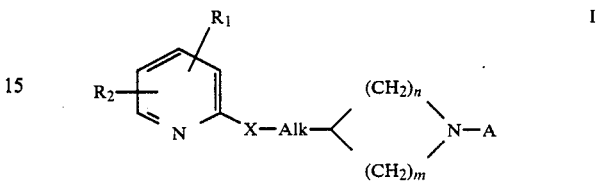

wherein the radicals $R_1$ and $R_2$ are the same or different and represent hydrogen, halogen atoms, a trifluoromethyl group, a cyano group, a nitro group, an amino group, a mono-$C_1$-$C_6$-alkylamino group, a di-$C_1$-$C_6$-alkylamino group, an amino group that is substituted by a phenyl-$C_1$-$C_4$-alkyl radical or a halogenphenyl-$C_1$-$C_4$-alkyl radical, a $C_2$-$C_6$-alkanoylamino group, a $C_1$-$C_6$-alkoxycarbonylamino group, a $C_1$-$C_6$-alkyl group optionally substituted by a phenyl radical, a hydroxy group, a $C_1C_6$-alkoxy group, a $C_2$-$C_6$-alkanoyloxy group, a phenoxy group or a carbamoyl group optionally substituted by one or two $C_1$-$C_6$-alkyl groups, the radical A represents the group $$-CO-CH-R_3$$
$$\phantom{-CO-CH-}|$$
$$\phantom{-CO-CH}NR_4R_5$$

wherein $R_3$ is hydrogen, a phenyl radical, an indolyl-(3)-methyl radical, imidazolyl-(4)-methyl radical, a $C_1$-$C_{10}$-alkyl group, or wherein $R_3$ represents a $C_1$-$C_{10}$ alkyl group which is substituted by a carboxy group, a $C_1$-$C_6$-alkoxy-carbonyl group, an aminocarbonyl group, a hydroxy group, a $C_1$-$C_6$-alkoxy group, a $C_2$-$C_6$-alkanoyloxy group, a mercapto group, a $C_1$-$C_6$-alkylthio group, a $C_2$-$C_6$-alkanoyl mercapto group, a phenyl group, a hydroxyphenyl group, a dihydroxyphenyl group, an amino-$C_1$-$C_6$-alkylthio group, an amino-$C_1$-$C_6$-alkyloxy group, an amino group, a ureido group (H$_2$NCONH—) or a guanidino group or where $R_3$ together with the structural portion >CH(NHR$_4$) represents the pyrrolidine-2-yl radical (proline radical) or the 4-hydroxy-pyrrolidine-2-yl radical, $R_4$ is hydrogen, benzyl or a $C_1$-$C_6$-alkyl radical, $R_5$ is hydrogen, benzyl, a $C_1C_6$-alkyl radical, a $C_2$-$C_6$-alkanoyl radical or the group

wherein $R_3$ and $R_4$ have the already stated meanings and $R_6$ is hydrogen, benzyl or $C_2$-$C_6$-alkanoyl, X is oxygen, sulphur, SO or SO$_2$, Alk is alkylene with 0–4 carbon atoms and n and m are the same or different and can represent the numbers 1–3, provided that n can also be 0 when Alk is alkylene with at least one carbon atom and m represents in this case the numbers 2-6, their pyridine-N-oxides and/or aminoxides and physiologically acceptable salts thereof.

The alkyl groups, alkoxy groups, alkylamino groups, alkanoylamino groups, alkanoyloxy groups, alkanoylmercapto groups or quite generally alkanoyl groups shown in Formula I can be straight or branched. The same also applies to alkyl and alkyloxy groups (i.e., alkoxy groups) should these be a component of other groups (for example in the form of a monoalkyl or dialkylamino group, alkanoylamino group, alkoxycarbonylamino group, carbalkoxy group, alkylcarbonyl group, aminoalkyloxy group and analogous groups. This also applies to the phenyl-$C_1$-$C_4$-alkyl radical (group) wherein the alkyl part, should this consist of 2-4 carbon atoms, may also be straight or branched. In the case of the halogen atoms, these may be chlorine, bromine or fluorine, in particular chlorine and fluorine. The alkyl and alkoxy groups as such or as components of other groups consist in particular of 1-4 carbon atoms, preferably 1 or 2 carbon atoms. Alkanoyl groups, such as for example, alkanoylamino groups, alkanoyloxy groups or alkanoyl mercapto groups consist in particular of 2-4, preferably 2-3 carbon atoms. The alkyl part of the phenyl-$C_1$-$C_4$-alkyl radical (group) consists in particular of 1-3, preferably 1 or 2 carbon atoms. The group

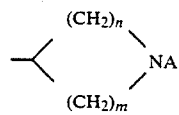

forms in particular a 5-, 6- or 7-membered ring.

Examples of such rings are: piperidine ring (piperidyl-(4)-, piperidyl-(3)- or piperidyl-(2)-ring), homopiperidine ring (for example homopiperidyl-(4)-ring), pyrrolidine ring (pyrrolidyl-(2)- or pyrrolidyl-(3)-ring).

X preferably represents sulphur.

Particularly important are those compounds of Formula I wherein X is sulphur, one of the radicals $R_1$ or $R_2$ is hydrogen and the saturated nitrogen-containing ring is a piperidyl radical that is directly linked to the sulphur atom (Alk=0 carbon atoms, i.e. Alk is absent) and $R_3$ represents hydrogen, phenyl, phenyl-$C_2$-$C_4$-alkyl, a straight or branched $C_1$-$C_6$-alkyl group which can also contain a mercapto group, a $C_1$-$C_4$-alkylmercapto group, an amino group, a carboxy group, a guanidino group or the group —$CONH_2$. In such cases the pyridine ring preferably contains a substituent corresponding to the given meanings for $R_1/R_2$, this substituent is preferably a halogen atom (for example chlorine), a trifluoromethyl group or a $C_1$-$C_6$-alkyl group (for example $CH_3$), which is in particular located in the 6 position of the pyridine ring. Should Alk be present, this group consists in particular of 1 or 2 carbon atoms $R_3$ is for example a $C_1$-$C_6$-alkyl group which contains in the 1-, 2-, 3-, 4-, 5- or 6-position (counting always begins at the point where the alkyl radical is linked to the radical molecule) an amino group (in particular in 3 or 4-position), a mercapto or hydroxy group (in particular in 1-or 2-position), an amino-$C_2$-$C_4$-alkylthio group, an amino-$C_2$-$C_4$-alkoxy group, a carboxy group, a $C_1$-$C_6$-alkoxycarbonyl group, a ureido group or a guanidino radical. For example the group —CO—CH($NR_4R_5$)—$R_3$ or —CO—CH($NR_4R_6$)—$R_3$ is based on the following amino acids: asparaginic acid (DL-form), asparagin, α-amino-butyric acid, leucine, isoleucine, ethyl asparaginate (L-form), citrulline ($H_2N$—CO—NH—($CH_2$)$_3$—CH($NH_2$)—$CO_2H$, L-form), ornithine (L-form), arginine, 4-thialysine ($H_2N$—$CH_2$—$CH_2$—S—$CH_2$—CH($NH_2$)—COOH), 2,6-diamino-oenanthic acid (ε-methyllysine), 4-oxalysine ($H_2N$—$CH_2CH_2$—O—$CH_2$—CH($NH_2$)COOH), glycine, N-methylglycine, N,N-dimethylglycine, proline, hydroxyproline, alanine, β-alanine, 3,4-dihydroxyphenylalanine, phenylalanine, tyrosine, tryptophan, cysteine, homocysteine (DL-form), methionine, penicillamine, lysine (in particular L-lysine), valine, valinemethylester (L-form), threonine, histidine, serine, homoserine, glutamic acid, glutamine, α,β-diaminopropionic acid, sarcosine, ethionine, α,β-diaminobutyric acid (L-form), α-aminoadipic acid (L-form).

Particularly beneficial effects are, for example, displayed by compounds of the following formula:

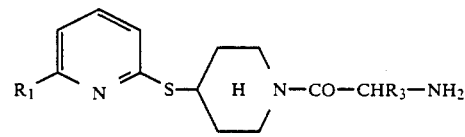

wherein $R_1$ is chlorine, bromine, fluorine or $CF_3$ and $R_3$ is hydrogen, phenyl, benzyl or $C_1$-$C_6$-alkyl, wherein the $C_1$-$C_6$-alkyl radical can also contain a mercapto group, a $C_1$-$C_4$-alkylmercapto group, a hydroxy group or a $C_1$-$C_4$-alkoxy group.

In accordance with the manufacturing process hydroxy-, mercapto and/or primary or secondary amino groups present in the products of the process can be alkylated or acylated.

The alkylation occurs for example through reaction with compounds of the formulae MHal, $ArSO_2OM$ and $SO_2(OM)_2$, wherein Hal is a halogen atom (in particular chlorine, bromine or iodine) and Ar is an aromatic radical (for example a phenyl or naphthyl radical optionally substituted by one or several lower alkyl radicals and M is a $C_1$-$C_6$-alkyl radical, a phenyl-$C_1$-$C_4$-alkyl radical, a halogen phenyl-$C_1$-$C_4$-alkyl radical or an amino-$C_1$-$C_6$-alkyl radical with protected amino group. Examples are p-toluene sulphonic acid-$C_1$-$C_6$-alkyl esters, $C_1$-$C_6$-dialkylsulfates, $C_1$-$C_6$-alkylhalides and the like. In the compounds mentioned above the alkyl group can be straight or branched. The alkylation and acylation reaction is optionally conducted under addition of conventional acid-binding agents, such as alkali metal hydroxides, alkali metal carbonates, alkali metal hydrogencarbonates, alkaline earth carbonates, alkali et al acetates, tertiary amines (such as trialkylamines such as triethylamine), pyridine or also alkalihydrides at temperatures between 0° and 200° C., preferably 40° and 140° C. in inert solvents or suspension agents. Solvents and dispersion agents that may, for example, be used are: aromatic hydrocarbons such as, for example, benzene, toluene, xylene; aliphatic ketones such as, for example, acetone, methylethyl ketone; halogenated hydrocarbons such as, for example, chloroform, carbon tetrachloride, chlorobenzene, methylene chloride; aliphatic ethers such as, for example, butyl ether; cyclic ethers such as, for example, tetrahydrofuran, dioxane; sulphoxides such as, for example, dimethyl sulphoxide; tertiary acid amides such as, for example, dimethyl formamide, N-methyl-pyrrolidone, hexamethyl phosphoric acid triamide; aliphatic alcohols such as methanol, ethanol, isopropanol, amyl alcohol, tert.-butanol, cycloaliphatic hydrocarbons such as cyclohexane and similar materials. Aqueous mixtures of the solvents named can also be used. Working is frequently at the reflux temperature of the solvent or dispersing agent used. The alkylating reaction components are frequently used in excess. The alkylation can also be carried out in the presence of tetra-alkyl ammonium salts (in particular the halides) in combination with alkali metal hydroxides at temperatures between 0°–100° C., preferably 20°–80° C., in an aprotic solvent or also in chloroform or methylene chloride. Aprotic solvents that may, in particular, be used are: tertiary amides (dimethyl formamide, N-methyl pyrrolidine, hexamethyl phosphoric acid triamide), dimethyl sulphoxide, acetonitrile, dimethoxy ethane, acetone, tetrahydrofuran.

During acylation a $C_2$–$C_6$-alkanoyl group, a $C_1$–$C_6$-alkylcarbonyl group, a carbamoyl group optionally substituted by one or two $C_1$–$C_6$-alkyl radicals or the group —CO—CH($NR_4R_6$)—$R_3$ is, for example, added. The procedure known per se is used, preferably using the corresponding halides (for example carb-$C_1$–$C_6$-alkoxy halides, $C_2$–$C_6$-alkanoyl halides), the corresponding anhydrides or also using the corresponding acids in the presence of known condensation agents [see, for example, process a)]. The reaction temperatures lie, for example, between 30° and 120° C.

It is optionally possible in the case of the alkylation and the acylation to proceed in such a manner that one first prepares an alkali metal compound (sodium, potassium or also lithium salt, for example) of the compound to be alkylated or acylated by reacting them in an inert solvent such as dioxane, dimethyl formamide, benzene or toluene with an alkali metal, alkali metal hydride or alkali metal amide (in particular sodium or sodium compounds) or butyl lithium at temperatures between 0° and 150° C. and then adding the alkylating agent.

In place of the alkylating and acylating agents it is also possible to use other chemically equivalent agents commonly used in chemistry (see, for example, L. F. and Mary Fieser "Reagents for Organic Synthesis", John Wiley and Sons Inc., New York, 1967, Vol. 1, pages 1303–1304 and Vol. 2, page 471).

The starting materials used for the process of the invention may contain hydroxy groups, mercapto groups, carboxy groups, amino groups or $C_1$–$C_6$-alkylamino groups that are protected by conventional protecting groups.

These are conventional protecting groups that are easily split off by hydrolysis or hydrogenolysis and are split off during or after the reaction. These are, protecting groups as set out, for example, in the book by J. F. W. McOmie, Protective Groups in Organic Chemistry, Plenum Press, Ney York, 1973, pages 43–143 as well as 183–215.

Should such protecting groups not be split off during the process reaction, the splitting off then occurs after the reaction. The starting compounds frequently already contain such protecting groups as a result of their manufacture.

These protecting groups are, for example, acyl groups that are easily cleavable solvolytically or groups that are cleavable by hydrogenation. The solvolytically cleavable protecting groups are, for example, cleaved by saponification with dilute acids (for example acetic acid, perchloric acid, hydrochloric acid, sulphuric acid, formic acid, trifluoroacetic acid) or by means of basic substances (potashes, soda, aqueous alkali metal solutions, alcoholic alkali metal solutions, $NH_3$) at temperatures between $-50°$ and 150° C., in particular between 0° and 100° C. Groups cleavable by hydrogenation such as arylalkyl radicals (benzyl radical) or aralkylcarbonyl radicals (carbobenzoxy radical) are appropriately cleaved by means of catalytic hydrogenation in the presence of conventional hydrogenation catalysts (precious metal catalysts), in particular palladium catalysts or also platinum catalysts (platinum oxide) or Raney nickel, in a solvent or suspension agent, optionally under increased pressure (for example 1–50 bar) at temperatures between 20°–150° C., in particular 30°–100° C., preferably 40°–80° C. Solvents or suspension agents that may, for example, be considered for the cleaving of such protecting groups are, for example: water, lower aliphatic alcohols, cyclic ethers such as dioxane or tetrahydrofuran, aliphatic ethers, halogenated hydrocarbons, dimethylformamide and so on, as well as mixtures of these agents. Protecting groups that can be cleaved by hydrogenation are, for example: benzyl radical, α-phenylethyl radioal, benzyl radical substituted in the benzene nucleus (p-bromine or p-nitrobenzyl radical), carbobenzoxy radical or carbobenzthio radical (whereby in such radicals the benzene nucleus can also be substituted, for example by $NO_2$), tert.-butyloxycarbonyl radical. Examples of hydrolytically cleavable radicals are: phthalyl radical, trityl radical, p-toluenesulfonyl radical, tert.-butyloxycarbonyl radical, tert.-butyl radical, dimethylethylene radical and similar groups, as well as lower alkanoyl radicals such as acetyl radical, propionyl radical, trifluoroacetyl radical, formyl radical and similar groups.

Should the starting materials contain free carboxy groups it is often appropriate to esterify these beforehand, for example with benzyl alcohol or another lower aliphatic alcohol (1–16, in particular 1–3 carbon atoms). In the end products such as ester groups can be cleaved by means of bases, for example alcoholic alkali lye, (for example methanolic KOH) or optionally also by means of mineral salts such as hydrochloric acid or sulphuric acid in alcoholic or aqueous alcoholic solution at temperatures between 20° and 100° C. by means of hydrogenation. Consideration may be given in particular to the conventional protecting groups used in peptide synthesis and the cleaving processes conventionally used therein. Inter alia reference is also made in this context to the book by Jesse P. Greenstein and Milton Winitz "Chemistry of Amino Acids", New York, 1961, John Wiley and Sons Inc., Volume 2, for example page 883 and following. The carbalkoxy group (for example low molecular) may also be considered.

The conversion of compounds of Formula I into the corresponding amine-oxide and/or the pyridine-N-oxide may, for example, be carried out in inert solvents such as chloroform or other hydrocarbons, benzene, toluene, acetone, dilute acetic acid or ethyl acetate with hydrogen peroxide, a conventional aliphatic or aromatic peracid (peracetic acid, perbenzoic acid, m-chloroperbenzoic acid) or other mono substitution products of hydrogen peroxide such as alkali peroxides or alkyl peroxides (for example tert.-butyl peroxide) at temperatures between 0° and 150° C., preferably 0° to 100° C. Should X=S, the corresponding sulphoxides or sulfones will first be formed here. These can, however, then be further oxidized to the aminoxides.

The transformation of compounds of Formula I, wherein X is a sulphur atom, into such compounds where X is the group SO or SO$_2$ is also effected by oxidation in a manner which is per se known. Oxidation agents that can be used successfully are, for example, hydrogen peroxide, dinitrogen tetroxide, potassium permanganate, peracids (for example perbenzoic acid, monoperphthalic acid, peracetic acid), nitric acid, chromic acid or other known oxidation agents. It is appropriate to carry out this conversion in the presence of water or of solvents, for example, alcohols, acetic acid (glacial acetic acid), acetic acid ethyl ester, benzene, acetone or chloroform).

In particular the lower alcohols, for example methanol or also acetic acid are well suited. In the case of oxidation with 30% hydrogen peroxide, peracids, nitric acid, nitrous gases (nitrogen dioxide) under cooling, for example at temperatures between $-20°$ C. and $+20°$ C. there is generally obtained, as a main product, the corresponding sulphoxide as well as small amounts of the sulphone. Then it is possible to produce corresponding sulphoxides from compounds of Formula I, wherein X=S, by means of oxidation with chromic acid (for example in acetic acid solution at temperatures between 50°–100° C.), by means of oxidation with, for example, iodosobenzene or through treatment with bromine (for example in a halogenated hydrocarbon such as chloroform or carbon tetrachloride under cooling) and subsequent hydrolysis of the dibromine derivative by means of water or dilute alkali lye. With regard to the reaction conditions and to other oxidation agents, reference is made, for example, to Houben-Weyl, Methoden der Organischen Chemie, Volume IX (1955), pages 211–218. Oxidation of sulphides of L Formula I (X=S) with dimethyl sulphoxide at higher temperature (150°–180° C.) according to the teaching of J.Org.-Chem. Vol 23 (1958), pages 2028–2029 is also possible.

The sulphones and sulphoxides obtained in each case can be separated by means of conventional separation processes, for example, by column chromatography in silica gel.

Using stronger oxidation agents such as, for example, potassium permanganate in acetic acid or aqueous sulphuric acid solution at temperatures between 50° and 100° C. the corresponding sulphone is obtained in larger yield or as the main product. The oxidation of compounds of Formula I wherein X=S or SO can, for example, also be effected by means of hydrogen peroxide or peracids at higher temperature, such as for example 80°–120° C. (in acetic acid solution or in glacial acetic acid and acetic acid anhydride, in the presence of phosphoric acid or another conventionally used inert agent), by means of chromic acid, by means of anodic oxidation or optionally also by means of sodium hypochlorite solutions (see Houben-Weyl, Methoden der Organischen Chemie, Volume IX (1905), pages 227–231). Another possibility is oxidation with organic hydroperoxides (for example alkylhydroperoxides such as tert.-butylhydroperoxide) in the presence of vanadium, molybdenum or titanium compounds (for example oxides of the metals named such as molybdenum dioxide, vanadium pentoxide) in organic solvents such as aromatic hydrocarbons (benzene), alkanols (ethanol) or esters of aliphatic carboxylic acids with alkanols (ethyl acetate) at temperatures between 40°–120° C., preferably 50°–80° C., according to the disclosure in Angewandte Chemie 78 (1966), page 937.

Those compounds of Formula I which contain asymmetric hydrocarbon atoms and generally occur as racemates can be cleaved in a manner which is known per se, for example with the aid of an optically active acid into the optically active isomers. It is, however, also possible to use from the outset an optically active starting substance, so that the end product is then obtained in a correspondingly optically active or diastereomeric form.

The present invention also comprises the D and L forms as well as the DL mixture in the event that the compound of Formula I has an asymmetric carbon atom and, also the corresponding diastereomeric forms, in the event that there are two and more asymmetric carbon atoms.

Depending on the conditions of the process and the starting materials, the final substances of Formula I are obtained in free form or in the form of their salts. The salts of the final substances can be reconverted into the bases in a manner which is known per se, for example with alkali or ion exchangers. Of the latter, salts may be obtained through reaction with organic or inorganic acids, in particular with those that are suitable for the formation of therapeutically active salts.

The therapeutically active salts may, for example, be the salts with following acids: hydrohalic acids (HCl, HBr), sulphuric acid, phosphoric acids, nitric acid, perchloric acid, organic mono-, di- or tri-carboxylic acids of the aliphatic, alicyclic, aromatic or heterocyclic series as well as sulfonic acids. Examples of such acids are: formic, acetic, propionic, succinic, glycolic, lactic, malic, tartaric, citric, ascorbic, maleic, fumaric, hydroxymaleic, gluconic or pyruvic acid; phenyl acetic acid, benzoic acid, p-aminosalicylic acid, embonic acid, methanesulphonic, ethanesulphonic or hydroxyethanesulphonic acid; ethylenesulphonic acid; halobenzenesulphonic, toluenesulphonic or naphthalenesulphonic acid, sulphanilic acid or also 8-chloro-theophylline.

The compounds of the invention are suitable for the preparation of pharmaceutical compositions. The pharmaceutical compositions or medicaments can contain one or several of the compounds of the invention. Conventional pharmaceutically acceptable carriers and ancillary substances may be used for the production of the pharmaceutical formulations.

With regard to the process (a):

The process is conducted at temperatures between 0° and 150° C., preferably 40° and 100° C. in inert solvents or suspension agents. Solvents or dispersing agents that may, for example, be used are: aromatic hydrocarbons optionally substituted by chlorine or bromine, such as for example benzene, toluene, xylene, chlorobenzene, pyridine; low molecular aliphatic ketones (for example 3–6 carbon atoms) such as, for example acetone, methylethylketone; halogenated hydrocarbons such as, for example, chloroform, carbon tetrachloride, chlorobenzene, methylene chloride; low molecular aliphatic ethers (for example 4–10 carbon atoms) such as dimethoxyethane, butylether; saturated cyclic ethers such as, for example, tetrahydrofuran, dioxane; sulphoxides such as, for example, dimethyl sulphoxide; tertiary acid amides such as, for example, dimethylformamide, tetramethyl urea, N-methylpyrrolidine, hexamethylphosphoric acid triamide; acetonitrile; low molecular aliphatic alcohols such as methanol, ethanol, isopropanol, amyl alcohol, tert.-butanol; cycloaliphatic hydrocarbons such as cyclohexane; low molecular saturated chlorinated and fluorinated hydrocarbons which contain 1–5 carbon atoms, in which case the individual carbon atoms may be substituted with one or more (2 to 3) chlorine and/or fluorine atoms, such as chloroform, methylene chloride. It is also possible to use aqueous mixtures of the solvents mentioned. Working is frequently at the reflux temperature of the solvents or dispersing agents used.

Optionally it is also possible to proceed by first producing from compound II an alkali metal compound (sodium, potassium or also lithium salt for example) by allowing this to react in an inert solvent such as dioxane, dimethylformamide, benzene or toluene with an alkali metal, alkali hydride or alkali amides (in particular sodium or sodium compounds) or butyl lithium at temperatures between 0° and 100° C. and then reacting with compound III (for example in the form of the acid halide).

Should the free acid of Formula III be used, its may be activated through the presence of condensation agents such as dicyclohexylcarbodiimide, sulphurous acid-bis-alkylamides (for example $SO[N(CH_3)_2]_2$), N,N'-carbonyldiimidazole and the like (See Organic Reactions, Vol. 12, 1962, pages 205 and 239).

If an acid of Formula III with an activated carboxyl group is used in process a) these should advantageously be compounds of the general formula

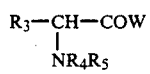    VI wherein $R_3$, $R_4$ and $R_5$ have the meanings given previously and W is a halogen atom, a group of formula —OR', —SR' or a group of formula —OCO—R" and R' represents a $C_1$-$C_6$-alkyl radical or, in the case of —OR' or —SR' also a phenyl radical, a phenyl radical substituted by nitro groups, $C_1$-$C_4$-alkoxy groups, $C_1$-$C_4$-alkyl groups or halogen atoms (chlorine, fluorine, bromine), a cyanomethyl radical or a carboxymethyl radical and R" is a straight or branched $C_1$-$C_6$-alkyl radical, a $C_1$-$C_6$-alkoxy radical, a phenoxy radical or a carbobenzoxy radical or also the radical $R_3$—CH(NR$_4$R$_5$)—.

Should W represent a halogen atom, this should preferably be chlorine, bromine or iodine; should R' or R" represent alkyl radicals or alkoxy radicals, then these are preferably of low molecular weight and consist of 1–4 carbon atoms.

Frequently, particularly when W (Formula VI) is a halogen atom or the group —OCOR", it is appropriate to have present acid-binding materials such as alkali hydroxides, alkali carbonates, alkali hydrogen carbonates, alkali acetates, alkaline earth carbonates, trialkylamines, dialkylamines, pyridine and similar materials, or also surplus compound II. Here, the acid-binding agent can also be simultaneously used alone or mixed with other conventional agents as solvent (for example pyridine). Care should be taken that any non-converted starting substance III or VI, in particular should an acid chloride be involved, is carefully neutralized and removed. It is frequently advisable to effect chromatographic purification of the reaction product over silica gel, with for example elution with a chloroform-ethanol mixture (ethanol content for example 4%) optionally with the addition of aqueous ammonia.

In place of the listed activating agents for the carboxyl group it is also possible to use other chemically equivalent agents conventionally used in chemistry. Such agents and processes are, for example, listed in the following literature sources: L. F. and Mary Fieser "Reagents for Organic Synthesis", John Wiley and Sons Inc., New York, 1967, Vol. 1, pages 1303–1304 and Vol. 2, page 471); Jakubke, Jeschkeit, "Aminosäuren, Peptide, Proteine", Akademie-Verlag, Berlin, 1982, 2nd Edition, pages 158–183. The previously mentioned literature sources and their content as set out in the pages referred to are incorporated herein by reference.

With regard to process (b):

The process for the manufacture of compounds of Formula I from compounds of Formula IV and V is carried out in a solvent or dispersing agent at temperatures between 20° and 200° C., preferably 40° and 150° C., in particular 50° and 120 C. Solvents and dispersing agents that may, for example, be used are: lower aliphatic alcohols (1–6 carbon atoms); propanol, isopropanol, butanol, lower aliphatic ethers (diethylether, diisopropylether), aromatic hydrocarbons (benzene, toluene, xylene), cyclic ethers (dioxane, tetrahydrofuran), esters of lower aliphatic carboxylic acids with lower aliphatic alcohols, amides and N-alkylsubstituted amides of aliphatic $C_1$-$C_4$-carboxylic acids (dimethylformamide, dimethylacetamide), $C_1$-$C_6$-dialkyl sulphone (dimethyl sulphone, tetramethylene sulphone), $C_1$-$C_6$-dialkyl sulphoxides (dimethyl sulphoxide) as well as other aprotic agents such as N-methylpyrrolidone, tetramethylurea, hexamethylphosphoric acid triamide, acetonitrile. The individual alkyl radicals of the above listed solvents contain, for example, 1–6, in particular 1–4 carbon atoms.

The process is appropriately conducted in the presence of condensation agents. Condensation agents that may, for example, be used are: inorganic condensation agents such as alkali metal or alkaline earth metal hydroxides, alkali metal hydrides, alkali metal amides, alkali metal or alkali earth metal carbonates or organic bases such as pyridine, tertiary amines, piperidine, alkali metal alcoholates, alkali metal acetates or also triethylphosphate. The alkali metals are, in particular, sodium or potassium. Working may also be under phase-transfer conditions (i.e. under addition of one or several long-chain amines such as a benztributylammoniumhalide, a tetrabutyl-ammonium-halide or benzyltriphenyl-phosphonium chloride).

The starting materials of Formulas IV and V can also be used in the form of their salts.

Generally one commences by preparing the appropriate salt from the starting component which contains the hydroxy or mercapto group, first by using one of the above-listed alkali metal compounds and then subsequently reacts this with the second reaction component. The amino group as well as other amino, hydroxy and/or mercapto groups optionally present in the starting component of Formula V is preferably protected by conventional protective groups. Such protecting groups can be cleaved solvolytically or by hydrogenation after the completion of the reaction.

Should Y of Formula V be a $C_1$-$C_6$alkyl-sulfonyloxy group, this is advantageously one with 1–4 carbon atoms in the alkyl portion (for example the methylsulfonyloxy group). Should Y of Formula V be an arylsulfonyloxy group, the aryl radical is advantageously a phenyl or naphthyl radical, which may be optionally substituted by $C_1$-$C_4$-alkyl radicals (in particular methyl radicals), (for example p-toluenesulfonyloxy group).

Starting materials of Formula V can be obtained from the known compounds of Formula V, wherein the group $R_3$—CH(NR$_4$R$_5$)—CO— is hydrogen, through introduction of the previously named radical by N-acylation in a method which is known per se or according to the conditions set out in this description for process (a).

From compounds of Formula V, wherein Y is the hydroxy group, it is possible to obtain starting substances of Formula V wherein Y is a halogen atom, for example, through reaction with thionylhalides (chlorides, bromides, iodides) or sulphonic acid chlorides in halogenated hydrocarbons (chloroform) or aromatic hydrocarbons (benzene) or in pyridine at temperatures between 20° and 150° C. (preferably at the boiling temperature of the solvent used). Starting materials of Formula V, wherein Y is an alkylsulfonyloxy group or an arylsulfonyloxy group, can, for example be obtained from the corresponding hydroxy compounds (Y=OH) by reaction with $C_1$-$C_6$-alkyl-sulphonic acid chlorides or the corresponding arylsulphonic acid chlorides in inert solvents conventionally used for that purpose (benzene, toluene, xylene, chloroform, methylene chloride, dioxane) at temperatures between 20°-150° C. The process is advantageously carried out in the presence of an acid-binding substance (for example tertiary amines such as triethylamine).

In all of these cases, the amino groups present as well as optionally other hydroxy or mercapto groups present are protected by readily cleavable protective groups.

It is, for example, possible to obtain starting materials of Formula V wherein Y is the mercapto group from the halides of Formula V (Y=halogen), through reaction with alkali sulphides. These reactions can be carried out according to the description of C. Ferri, Reactionen der organischen Synthese 1978, pages 205–209 or according to the description in German patent specification No. DE-OS 2 230 392, for example page 9.

Starting materials of Formula V having the following structure

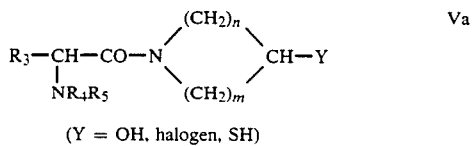

(Y = OH, halogen, SH)

can, for example, be obtained as follows:

A compound of Formula Va, wherein the grouping >CHY has the structure >C=O is reacted with hydrogen sulphide by analogy with the procedure described in H. Barrera and R. E. Lyle, J. Org. Chem. 27 (1962), pages 641–643 and subsequently reduced with sodium borohydride to compound Va, wherein Y=SH. It is, however, also possible in a compound Va (>CHY=CO) to reduce the keto group in known manner with alkali metal borates (Na, K, Li) or other complex metal hydrides (for example lithium aluminum hydride) to the hydroxy group (see Houben-Weyl, Methoden der Organischen Chemie, Volume 4/1d, 1981, page 271 et. seq.), to exchange the hydroxy group by means of conventional chlorinating agents (for example thionyl chloride, sulphuryl chloride) for a chlorine atom (see Houben-Weyl, Methoden der Organischen Chemie, Volume 5/3, 1962, pages 862–912), to produce the corresponding Grignard compound (Formula Va Y=MgCl) from the so-obtained chloride with magnesium (see Houben-Weyl Methoden der Organischen Chemie, Volume 13/2a, 1973, pages 53–85) and to produce from such a Grignard compound by means of sulphur or thionyl chloride (see Houben-Weyl, Methoden der Organischen Chemie, Volume 9, 1955, page 19; E. E. Reid, Organic Chemistry of Bivalent Sulfur, Vol. I Chem. Publ. Corp., New York, 1958, page 37) the mercapto compound Va, wherein Y=SH. Here, too, amino groups present as well as optionally present carboxy groups, hydroxy groups or mercapto groups are protected by corresponding protective groups.

Additional pharmacological and pharmaceutical data:

The compounds of the invention possess a good antinociceptive effect (i.e., in the electro-pain test in the mouse). For example, with the above-described experimental method a pronounced antinociceptive effect is recorded with an oral dosage of 10 mg/kg body weight in the mouse.

The lowest antinociceptively effective dosage in the above-mentioned animal experiment is, for example 2.5 mg/kg oral
1.25 mg/kg intraperitoneal
0.25 mg/kg intravenous The following can, for example, be considered as a general dosage range for the antinociceptive effect (animal experiment as above):

2.5–40 mg/kg oral, in particular 5–20
1.25–30 mg/kg intraperitoneal, in particular 2.5–15
0.25–5 mg/kg intravenous, in particular 0.5–2

The profile of the antinociceptive effect of the compounds of the invention is, for example, comparable to the effect of morphine, although in particular the following differences are apparent: it is not an opiate and therefore has no addiction and/or dependency potential of the opiate type.

The compounds of the invention are effective analgesics.

The pharmaceutical forms for the antinociceptive effect generally contain between 2.5 and 30, preferably 5 to 20 mg of the active components of the invention.

Administration may, for example, be in the form of tablets, capsules, pills, sugar-coated tablets, suppositories, ointments, gels, creams, powder, dusting powder, aerosols or in liquid form. Liquid forms of application may, for example, be oily or alcoholic or aqueous solutions as well as suspensions and emulsions.

The individual dosage of the active components of the invention may for example lie (a) in the oral medicinal forms between 2.5–30, preferably 5–20 mg
(b) in the parenteral medicinal forms (for example intravenous, intramuscular) between 0.5–6, preferably 1.0–3.0 mg.
(the doses are in each case the amount of free base and must be adjusted if a salt is used)

For example it is possible to recommend 3 times daily 1 to 3 tablets containing from 5 to 20 mg of active substance or, for example, in the case of intravenous injection 1 to 3 times daily one ampoule of 2 to 4 ml content with 1 to 4 mg of substance. In the case of oral administration the minimum daily dose is, for example, 10 mg; the maximum daily dose for oral administration for antinociceptive use should not exceed 600 mg.

The acute toxicity of the compounds of the invention in the mouse (expressed in the LD 50 mg/kg; method after Miller and Tainter: Proc. Soc. Exper. Biol. a. Med. 57 (1944) 261) is, for example, between 200 and 300 mg/kg (respectively above 250 mg/kg) in the case of oral administration.

The medicaments can be used in human medicine, veterinary medicine as well as in animal husbandry alone or mixed with other pharmacologically active substances.

In addition the compounds of the invention also possess a good antidepressant activity (demonstrated in the swimming test after Porsolt). For example in this experimental method a 50-80% activity is achieved with a dosage of 20 mg/kg body weight in the rat.

The lowest dosage to display antidepressant activity in the above mentioned animal experiment is, for example 10 mg/kg oral
5 mg/kg intraperitoneal
1 mg/kg intravenous The general dosage range that can, for example be considered for antidepressant activity (animal experiment as above) is:

10-60 mg/kg oral, in particular 20-40 mg
5-40 mg/kg intraperitoneal, in particular 10-30 mg
1-15 mg/kg intravenous, in particular 3-12 mg The profile of the antidepressant effect of the compounds of the invention is comparable with the effect of the known pharmaceutically-active ingredient imipramine, although displaying in particular the following differences thereto:

longer lasting effect, stronger effect, with predominantly stimulating (thymoretic) effect. The compounds of the invention are therefore also effective antidepressants.

The pharmaceutical formulations for the antidepressive effect generally contain between 1 to 200, preferably 10 to 100 mg of the active component of the invention.

Administration can, for example, be in the form of tablets, capsules, pills, coated tablets, suppositories, ointments, gels, creams, powder, dusting powder, aerosols or in liquid form. Liquid forms of application that may, for example, be used are: oily or alcoholic or aqueous solutions as well as suspensions and emulsions. Preferred forms of administration are tablets containing between 20 and 100 mg or solutions which contain between 0.1 and 0.5 percent by weight of the active substance.

The individual dose of the active components of the invention for the antidepressant effect can, for example, lie
(a) between 20-100 mg for oral medicinal forms
(b) between 1-10 mg for parenteral medicinal forms (for example intravenous, intramuscular)
(The doses are in each case are the amount of free base and must be adjusted if a salt is used)

For example it is possible to recommend 3 times daily 1 to 3 tablets having a content of 20 to 200 mg of active substance or, for example, for intravenous injection 1 to 3 times daily one ampoule of 2 to 4 ml content with 2 to 5 mg of substance. In the case of oral administration the minimum daily dosage is for example 20 mg; the maximum daily dosage in the case of oral administration for the antidepressant effect should not exceed 600 mg.

The invention is illustrated by the following examples.

EXAMPLE 1

[N-glycyl-piperidyl-(4)]-[6-chloro-pyridyl-(2)-]-sulphide

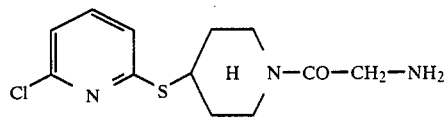

To a solution of 12.3 g (0.07 Mol) of N-tert.-butyloxycarbonyl glycine in 80 ml of dioxane there are added, as a single addition with stirring, 11 350 g (0.07 Mol) of 1,1-carbonyl diimidazole at room temperature.

The reaction commences with prolific development of $CO_2$. To complete the reaction, heat is applied for 30 minutes at 40° C. Following cooling to 20° C., a solution of 14.3 g (0.0624 Mol) pipericyl-(4)-[6-chloro-pyridyl-(2)]-sulphide dissolved is 20 ml of dioxan is added. The temperature rises to 35° C.

Heating continues for a further 3 hours at 45°-50° C. Thereafter the solvent is removed in a rotary evaporator, the oily residue is dissolved in 200 ml of ether and the solvent is shaken twice with 50 ml of water in each case. The ether phase is dried with $MgSO_4$, filtered and concentrated. The residue is dissolved in 60 mls of isopropanol and the solution acidified with isopropanolic hydrochloric acid. The mixture is subsequently heated for about 4 hours with stirring and under reflux. The solution is then concentrated, the residue is dissolved in ethanol and mixed with ether until turbidity commences. After being left to stand for 36 hours in a closed vessel at room temperature the crystallate is suction filtered, washed several times with a mixture of equal parts by volume of ethanol and ether and dried. Melting point of the hydrochloride: 146°-148° C. Yield: 7.6 g.

EXAMPLE 2

(L)-[N-alanyl-piperidyl-(4)]-[6-chloro-pyridyl-(2)-]-sulphide

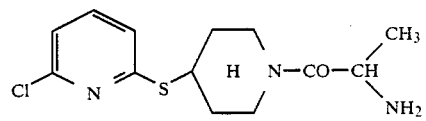

17.88 g of L-tert.-butyloxycarbonylalanine, dissolved in 150 ml of dioxane are added to 15.3 g of 1,1-carbonyldiimidazole. The reaction commences with prolific development of $CO_2$ and is completed by 30 minutes' heating to 40° C. The mixture is then cooled to room temperature again. Following addition of a solution of 21.6 g of piperidyl-(4)-[6-chloro-pyridyl-(2)-]-sulphide in 30 ml of dioxane the mixture is heated for 3 hours to 45°-50° C. The solvent is then removed in a rotary evaporator, the residue dissolved in 300 ml of ether and the solvent shaken twice with 70 ml of water in each case. The ether phase is dried with $MgSO_4$ filtered and evaporated. The residue is dissolved in 100 ml of isopropanol and the solvent acidified with isopropanolic hydrochloric acid. Following heating for four hours under reflux the solution is greatly concentrated. The residue is dissolved in ethanol, filtered and treated with ether until turbidity commences. The substance crystallizes spontaneously. The crystalline precipitate is suction filtered, washed with a mixture of equal parts by volume of ethanol and ether and dried. The hydrochloride melts at 195°-196° C. Yield: 20.3 g (64% of theory).

The compounds shown in Table 1 are prepared by a procedure which is analogous with the above examples. Compounds of the following formula are involved:

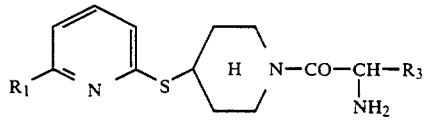

In each case 0.03 Mol of the protected amino acid (for example N.tert.-butyloxycarbonyl amino acid) with 0.025 Mol of piperidyl-(4)-[6-chloro-pyridyl-(2)]-sulphide in dioxane. Prior to taking up the reaction product in ether (i.e. after removal of the dioxane) it is optionally possible to treat with water (for example 50 ml of water).

In Example 8, the reaction solution is treated with 80 ml of water, shaken again with $CH_2Cl_2$. After separation of the methylene chloride phase, the organic phase is dried and the solvent is removed. The tert.-butyloxycarbonyl protecting group is then split off with hydrochloric acid in isopropanol.

The splitting off of the amino acid protecting group is effected in each case through heating with hydrochloric acid in isopropanol; duration 2 hours (for 3 hours in Example 3).

In the case of Examples 3 and 5 the isolation of the reaction product is effected in the form of the maleate. The maleate is prepared using maleic acid in acetone solution and separated off through addition of diethyl ether.

with 14.35 g of sodium chloride in 1.9 liters of water for injection purposes. The solution is made up to 2 liters with water for injection purposes, filtered through a membrane filter of pore size 0.2 μm and filled under sterile conditions into sterile ampoules of 2.15 ml each. One ampoule contains 10 mg of active substance in 2 ml of solution.

What is claimed is:

1. Compounds of the formula

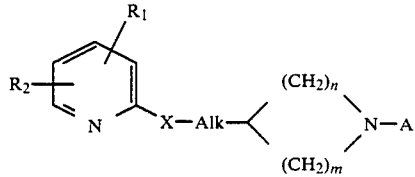

wherein the radicals $R_1$ and $R_2$ are the same or different and represent hydrogen, halogen atoms, a trifluoromethyl group, a cyano group, a nitro group, an amino group, a mono-$C_1$-$C_6$-alkylamino group, a di-$C_1$-$C_6$-alkylamino group, an amino group that is substituted by a phenyl-$C_1$-$C_4$-alkyl radical or a halogenphenyl-$C_1$-$C_4$-alkyl radical, a $C_2$-$C_6$-alkanoylamino group, a $C_1$-$C_6$-alkoxycarbonylamino group, a $C_1$-$C_6$-alkyl group optionally substituted by a phenol radical, a hydroxy group, a $C_1$-$C_6$-alkoxy group, a $C_2$-$C_6$-alkanoyloxy group, a phenoxy group or a carbamoyl group optionally substituted by one or two $C_1$-$C_6$-alkyl groups, the radical A represents the group

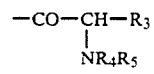

TABLE 1

| Example No. | $R_1$ | $R_3$ | Melting Point of the HCl salt °C. | Amino Acid Starting Compound | Reaction medium | Yield |
|---|---|---|---|---|---|---|
| 3 | Cl | —CH(CH$_3$)$_2$ | 160–161 (Maleate) | BOC-L-Valine | Dioxane | 6 g |
| 4 | Cl | —CH$_2$—CH(CH$_3$)$_2$ | 84 | BOC-L-Leucine (Hydrate) | Dioxane | 8.5 g |
| 5 | Cl | —(CH$_2$)$_3$—CH$_3$ | 149–150 (Maleate) | BOC-Norleucine | Dioxane | 6 g |
| 6 | Cl | —C$_6$H$_5$ | 240–242 D | BOC-Phenylglycine | Dioxane | 8 g |
| 7 | Cl | —CH$_2$—C$_6$H$_5$ | 120 | BOC-Phenylalanine | Dioxane | 7.4 g |
| 8 | Cl | —(CH$_2$)$_2$—SCH$_3$ | 92 | BOC-L-Methionine | CH$_2$Cl$_2$ (60 ml) | 2.5 g |
| 9 | Cl | —C(SH)(CH$_3$)$_2$ | 144 | BOC-D-Penicillamine | Dioxane | 4.5 g |

D = decomposition;
BOC = tert.butyloxycarbonyl

EXAMPLES OF PHARMACEUTICAL FORMULATIONS

Capsules with 100 mg of Active Ingredient 10 kg of active substance (compound according to Example 1 as hydrochloride) are granulated in a turbulence spray granulation apparatus with a solution composed of 0.25 kg of gelatin in 2.25 kg of water in the conventional manner. Following addition of 0.80 kg of corn starch, 0.1 kg of magnesium stearate and 0.05 kg of highly disperse silicon dioxide, the mixture is filled into size 3 hard gelatin capsules in filling batches of 112 mg in each case. Each capsule contains 100 mg of active substance

EXAMPLE FOR AMPOULES 20 g of active substance (compound according to Example 1 as hydrochloride) are dissolved together wherein $R_3$ is hydrogen, a phenyl radical, an indolyl-(3)-methyl radical, imidazolyl-(4)-methyl radical, a $C_1$-$C_{10}$-alkyl group, or wherein $R_3$ represents a $C_1$-$C_{10}$ alkyl group which is substituted by a carboxy group, a $C_1$-$C_6$-alkoxycarbonyl group, an aminocarbonyl group, a hydroxy group, a $C_1$-$C_6$-alkoxy group, a $C_2$-$C_6$-alkanoyloxy group, a mercapto group, a $C_1$-$C_6$-alkylthio group, a $C_2$-$C_6$-alkanoyl mercapto group, a phenol group, a hydroxyphenyl group, a dihydroxyphenyl group, an amino-$C_1$-$C_6$-alkylthio group, an amino-$C_1$-$C_6$-alkyloxy group, an amino group, a ureido group ($H_2NCONH$—) or a quanidino group or where $R_3$ together with the structural portion $>CH(NHR_4)$ represents the pyrrolidine-2-yl radical (proline radical) or the 4-hydroxy-pyrrolidine-2-yl radical, $R_4$ is hydrogen, benzyl or a $C_1$-$C_6$-alkyl radical, $R_5$ is hydrogen, benzyl, a $C_1$-$C_6$-alkyl radical, a $C_2$-$C_6$-alkanoyl radical or the group

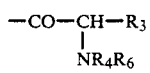

wherein $R_3$ and $R_4$ have the meanings stated above and $R_6$ is hydrogen, benzyl or $C_2$-$C_6$-alkanoyl, X is oxygen, sulphur, SO or $SO_2$, Alk is a direct bond or alkylene with 1-4 carbon atoms and n and m are the same or different and can represent the numbers 1-3, provided that n can also be 0 when Alk is alkylene and m represents in this case the numbers 2-6, their pyridine-N-oxides and/or aminooxides or a pharmaceutically-acceptable salt thereof.

2. A pharmaceutically composition which contains, as active ingredient, an effective amount of at least one compound according to claim 1 together with a conventional pharmaceutical carrier and/or diluent.

3. A method of treating a patient in need of analgesic, pain relieving or anti-depressant treatment, which comprises administering an effective amount of a compound according to claim 1.

* * * * *